(12) United States Patent
Thota et al.

(10) Patent No.: US 10,384,057 B2
(45) Date of Patent: *Aug. 20, 2019

(54) MULTI-LEAD MULTI-ELECTRODE MANAGEMENT SYSTEM

(71) Applicant: THE FLORIDA INTERNATIONAL UNIVERSITY BOARD OF TRUSTEES, Miami, FL (US)

(72) Inventors: Anil K. Thota, Miami Beach, FL (US); Ranu Jung, Miami Beach, FL (US); Sathyakumar S. Kuntaegowdanahalli, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 233 days.

This patent is subject to a terminal disclaimer.

(21) Appl. No.: 15/202,551

(22) Filed: Jul. 5, 2016

(65) Prior Publication Data

US 2017/0087353 A1 Mar. 30, 2017

Related U.S. Application Data

(63) Continuation of application No. 14/073,117, filed on Nov. 6, 2013, now Pat. No. 9,409,009.

(60) Provisional application No. 61/793,084, filed on Mar. 15, 2013, provisional application No. 61/724,690,
(Continued)

(51) Int. Cl.
*A61N 1/05* (2006.01)
*A61B 5/00* (2006.01)
*A61B 5/04* (2006.01)
*A61B 5/0488* (2006.01)

(52) U.S. Cl.
CPC ........ *A61N 1/0558* (2013.01); *A61B 5/04001* (2013.01); *A61B 5/0488* (2013.01); *A61B 5/04888* (2013.01); *A61B 5/4029* (2013.01); *A61B 5/6839* (2013.01); *A61B 5/6877* (2013.01); *A61N 1/05* (2013.01); *A61N 1/0507* (2013.01); *A61B 5/4076* (2013.01); *A61B 2562/0209* (2013.01); *A61B 2562/125* (2013.01); *A61B 2562/18* (2013.01); *A61B 2562/245* (2013.01); *Y10T 29/49208* (2015.01)

(58) Field of Classification Search
CPC .......... A61N 1/05; A61N 1/0558; A61B 5/04; A61B 5/04001; A61B 5/4029; A61B 5/6877
USPC .............................................. 607/2, 115, 116
See application file for complete search history.

(56) References Cited

U.S. PATENT DOCUMENTS

| | | |
|---|---|---|
| 3,699,956 A | 10/1972 | Kitrilakis et al. |
| 4,934,368 A * | 6/1990 | Lynch ................ A61N 1/36003 607/118 |
| 5,690,691 A | 11/1997 | Chen et al. |

(Continued)

FOREIGN PATENT DOCUMENTS

| | | |
|---|---|---|
| AT | 330342 B | 6/1976 |
| DE | 2437346 A1 | 2/1975 |

*Primary Examiner* — Christopher A Flory
(74) *Attorney, Agent, or Firm* — Marshall, Gerstein & Borun LLP

(57) ABSTRACT

A multi-lead multi-electrode system and method of manufacturing the multi-lead multi-electrode system includes a multi-electrode lead that may be used to deploy multiple separable electrodes to different spaced apart contact sites, such as nerve or muscle tissues, for example, that are spatially distributed over a large area.

17 Claims, 11 Drawing Sheets

Related U.S. Application Data filed on Nov. 9, 2012, provisional application No. 61/723,368, filed on Nov. 7, 2012.

(56) References Cited

U.S. PATENT DOCUMENTS

| | | | |
|---|---|---|---|
| 5,871,530 A * | 2/1999 | Williams | A61N 1/0563 607/122 |
| 6,038,472 A * | 3/2000 | Williams | A61N 1/0563 607/122 |
| 6,178,355 B1 * | 1/2001 | Williams | A61N 1/0563 607/122 |
| 6,281,262 B1 * | 8/2001 | Shikinami | A61L 17/12 264/230 |
| 6,505,075 B1 | 1/2003 | Weiner | |
| 6,999,819 B2 * | 2/2006 | Swoyer | A61N 1/0551 607/117 |
| 7,967,817 B2 | 6/2011 | Anderson et al. | |
| 7,983,755 B2 | 7/2011 | Starkebaum et al. | |
| 8,527,054 B2 | 9/2013 | North | |
| 9,409,009 B2 * | 8/2016 | Thota | A61N 1/05 |
| 2002/0143376 A1 | 10/2002 | Chinn et al. | |
| 2003/0212432 A1 * | 11/2003 | Khairkhahan | A61B 17/0057 606/200 |
| 2005/0267467 A1 * | 12/2005 | Paul | A61B 18/1402 606/41 |
| 2006/0206148 A1 * | 9/2006 | Khairkhahan | A61B 17/0057 606/213 |
| 2007/0255369 A1 | 11/2007 | Bonde et al. | |
| 2009/0192464 A1 * | 7/2009 | Axelsson | A61F 5/445 604/164.04 |
| 2009/0247018 A1 | 10/2009 | Kast et al. | |
| 2010/0023088 A1 * | 1/2010 | Stack | A61N 1/0558 607/44 |
| 2011/0166482 A1 * | 7/2011 | Stack | A61N 1/0558 601/2 |
| 2012/0035643 A1 * | 2/2012 | Khairkhahan | A61B 17/0057 606/194 |
| 2012/0071870 A1 * | 3/2012 | Salahieh | A61B 5/01 606/33 |
| 2012/0221014 A1 * | 8/2012 | Stack | A61N 1/0558 606/129 |
| 2013/0012982 A1 * | 1/2013 | Khairkhahan | A61B 17/0057 606/200 |
| 2013/0023724 A1 * | 1/2013 | Allen | A61F 2/0036 600/30 |
| 2013/0172973 A1 * | 7/2013 | Tockman | A61N 1/0556 607/118 |
| 2013/0317414 A1 * | 11/2013 | Shalon | A61F 5/0079 604/9 |
| 2013/0331759 A1 * | 12/2013 | Neisz | A61F 5/0076 604/8 |
| 2014/0128950 A1 * | 5/2014 | Thota | A61N 1/05 607/116 |
| 2014/0148842 A1 * | 5/2014 | Khairkhahan | A61B 17/0057 606/200 |
| 2015/0039021 A1 * | 2/2015 | Khairkhahan | A61B 17/0057 606/200 |
| 2015/0327979 A1 * | 11/2015 | Quinn | A61B 17/0057 606/200 |

* cited by examiner

MULTI-LEAD MULTI-ELECTRODE MANAGEMENT SYSTEM

RELATED APPLICATIONS

This application is a continuation of and claims priority from U.S. patent application Ser. No. 14/073,117, filed on Nov. 6, 2013, which is a non-provisional application that claims priority benefit of U.S. Provisional Patent Application No. 61/793,084, which was filed Mar. 15, 2013, of U.S. Provisional Patent Application No. 61/724,690, which was filed Nov. 9, 2012, and of U.S. Provisional Patent Application No. 61/723,368, filed Nov. 7, 2012. The entire specifications of each of U.S. patent application Ser. Nos. 14/073,117, 61/793,084, 61/724,690, and 61/723,368 are hereby incorporated by reference herein.

STATEMENT REGARDING FEDERALLY SPONSORED RESEARCH OR DEVELOPMENT

This invention was made with government support under Award or Contract No. N66001-12-C-4195 awarded by the Defense Advanced Research Projects Agency. The government may have certain rights in the invention.

FIELD OF THE DISCLOSURE

The present disclosure relates generally to a multi-lead multi-electrode system having multiple separable electrodes, methods, and components related thereto.

BACKGROUND

In the past decade, there have been significant advances in development of neurotechnology to stimulate neural and muscle tissue to replace lost function due to neurological disability or neutoruma. For example, there are commercially available systems for deep brain stimulation to treat symptoms of Parkinson's disease and other neuromotor and neuropsychological diseases; vagal nerve stimulation for treating some types if intractable epilepsies and depression, gastric stimulation for gastroparesis, stimulation of the peroneal nerve for foot drop, sacral nerve stimulation for urinary urge incontinence and incontinence, pacing of respiratory and abdominal muscles for respiratory insufficiency, and treatment of unmanageable and pathological pain in various sites of the body.

Most often, a single lead is used to target a single stimulation site, for example for vagal nerve stimulation. Here, there is a single electrode contact site connected via the lead to a stimulating device. In some instances a single lead contains multiple electrode contacts in concentric circles along its longitudinal axis placed at a pre-determined distances. Such a lead is used to stimulate close but longitudinally spatially separated excitable neural tissue, for example, for deep brain stimulation for treating Parkinson's disease spinal cord stimulation for pain management and inner ear (cochlear) stimulation for treating hearing loss. Since, in all of the above multi-electrode lead configurations the contacts are placed on an inseparable substrate at a predetermined distance, they cannot be used for stimulating multiple sites that are spatially distributed over a large 2-dimensional area such as for gastric stimulation.

Additionally, for some functional outcomes, multiple nerve or muscle tissues may have to be stimulated in a coordinated manner to achieve the best functional outcome. For example, for restoring respiration in high quadriplegic subjects and in other respiratory disorders, along with phrenic nerve multiple muscles that are spatially distributed need to be stimulated. In gastroparesis and in other gastric disorders, spatially distributed muscles and nerve endings need to be stimulated and/their activity needs to be sensed.

In addition, there have been attempts to provide sensory feedback to upper extremity amputees by stimulation of the peripheral nerves. Such peripheral nerve stimulation will also require multiple nerves to be targeted to provide information about multiple sensory sources and modalities to the amputee. In order to develop the next generation of neural driven prostheses for amputees, it will also be necessary to record multiple motor intents by recording from different sites, for example different peripheral nerves or muscle tissues. Some specific examples are discussed briefly hereinafter.

MedImplant Patent OS-PS330342, from September 1976, shows a system with a coiled lead of multiple connecting elements partially encased and then each individual connecting element is left free. Each individual connecting element is coiled. No protective bundling method is revealed.

U.S. Pat. No. 7,983,755 shows multisite gastric stimulation with multiple leads (Fig #4). However, U.S. Pat. No. 7,983,755 does not present a method for packaging such leads.

U.S. Pat. No. 5,690,691 shows multisite gastric stimulation with multiple lead. However, U.S. Pat. No. 5,690,691 does not present a method for packaging such leads.

U.S. Pat. No. 7,967,817 refers to a multi-electrode lead containing multiple electrode contacts in concentric circles along its longitudinal axis placed at a pre-determined distances.

U.S. Pat. No. 6,505,075 is an example for peripheral nerve stimulation to treat pain using longitudinal circular multi-contact lead.

U.S. Pat. No. 3,699,956 describes a percutaneous lead that provides fixation and minimizes bacterial penetration.

U.S. Patent Application Publication No. 2007/0255369 describes a percutaneous lead with flaps acting as anchors.

U.S. Pat. No. 4,934,368 describes two nerve cuff electrodes as a separate leads.

There is a need for a multi-electrode lead with separable electrode contacts to target nerve or muscle tissues that are spatially distributed over a large area.

SUMMARY

According to some aspects of the present disclosure, a multi-electrode lead and/or a packaging system for such a multi-electrode lead includes any one or more of the components described herein.

According to some aspects of the present disclosure, a multi-lead multi-electrode system includes any one or more of the components described herein.

According to some aspects of the present disclosure, a method of fabricating a multi-electrode lead includes any one or more of the fabrication steps described herein.

Additional optional aspects and forms are disclosed, which may be arranged in any functionally appropriate manner, either alone or in any functionally viable combination, consistent with the teachings of the disclosure. These and other aspects and advantages will become apparent upon consideration of the following detailed description.

DETAILED DESCRIPTION

This disclosure describes a multi-lead multi-electrode system that may be used to deploy multiple separable electrodes (contact sites) to different nerve or muscle tissues, for example, nerve or muscle tissues that are spatially distributed over a large area, and a process for packaging such a system.

A multi-electrode lead is defined as a longitudinal structure that can link a plurality of sensing or stimulating elements (electrodes) at its distal end to a stimulating or recording device or devices at its proximal end using connecting elements. Examples of connecting elements include metal wires that conduct electrical signals, ribbon cables that connect to an array of electrodes, optical fibers that conduct light, and similar devices. Preferably, the multi-electrode lead could be used as a lead across the skin connected to an external connector or device or as an implantable lead that connects to an implantable device.

Figure 1:
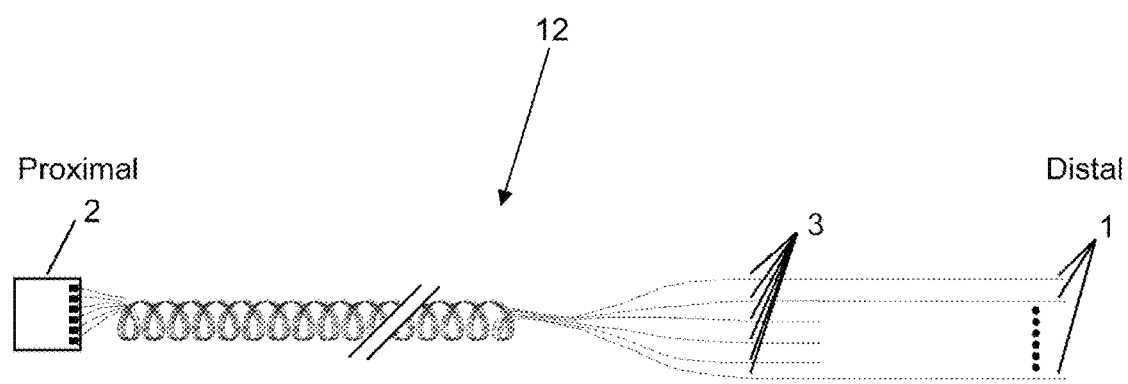
FIG. 1 illustrates a multi-electrode lead with one or more electrodes on one end, a stimulating or recording device on the other end, and one or more connecting elements.

Turning now to the drawings, FIGS. 1-8 illustrate a packaging system for a single multi-electrode lead. FIG. 1 illustrates a multi-electrode lead 12 with electrodes 1 on one end, or distal end, a stimulating or recording device 2 on the other end, or proximal end, and elongate connecting elements 3, such as wires and/or fiber optic strands, extending between the one end and the other end. The connecting elements 3 are coated with a thin film of biocompatible material that insulates it from the body fluids. The connecting elements 3 are secured together in a bundle between the proximal and distal ends. The bundle of connecting elements may be coiled over a partial length to provide strain relief and allow flexibility to the multi-electrode lead. In some instances this coiling may not be present. In some instances, connecting elements 3 outside the coil sheath 4 may individually be coiled. The electrodes 1 and the distal ends of the connecting elements 3 are separated or readily separable, i.e., not bundled or connected together or easily and readily separable such as along a frangible section or removable temporary connection, such that the electrodes may be placed on or in a patient in a spaced apart array to be operatively engaged with a plurality of spaced apart nerve or muscle tissues that are spatially distributed over a large area, such as to span multiple organs and/or muscle groups and/or nerve regions.

Figure 2:
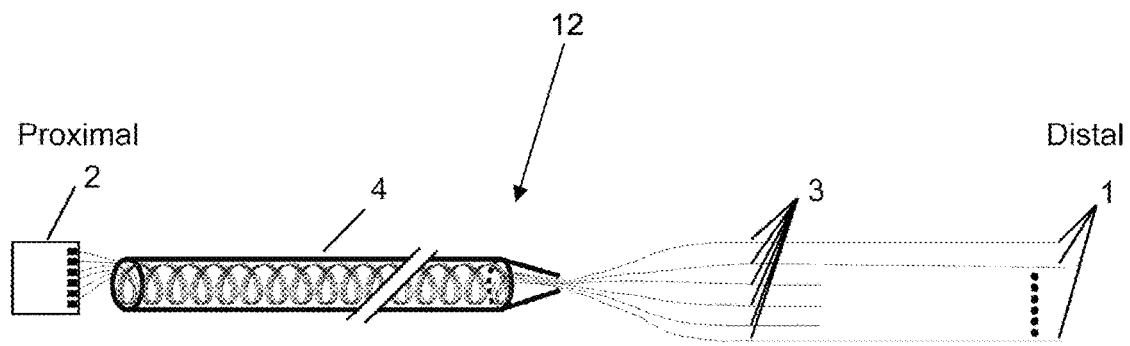
FIG. 2 illustrates a coiled portion of the multi-electrode lead ensheathed in a coil sheath along with electrodes, a stimulating or recording device, and connecting elements.

FIG. 2 illustrates the coiled portion of the multi-electrode lead 12 ensheathed, i.e., sheathed within, such as by being surrounded and at least partly encased within a sheath or casing, in a coil sheath 4. The coil sheath 4 is preferably formed of a tube of biocompatible material. The ensheathing element (e.g., the coil sheath 4) may extend beyond the coiled portion. The coil sheath keeps the coiled bundle in place.

Figure 3:
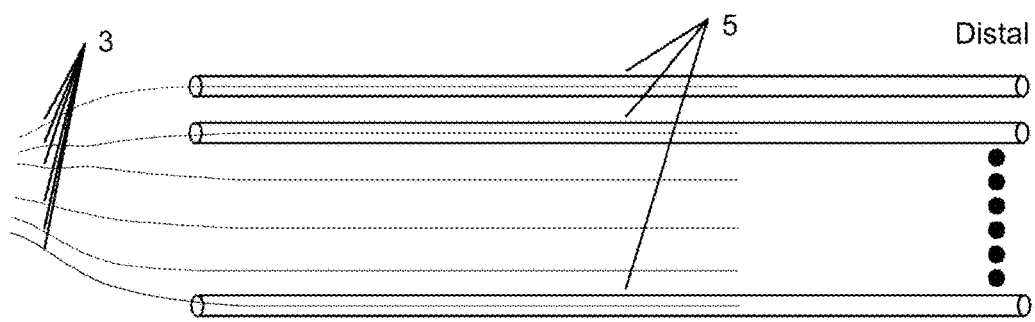
FIG. 3 illustrates individual connecting elements ensheathed separately by individual protective sheaths along with connecting elements.
Figure 4:
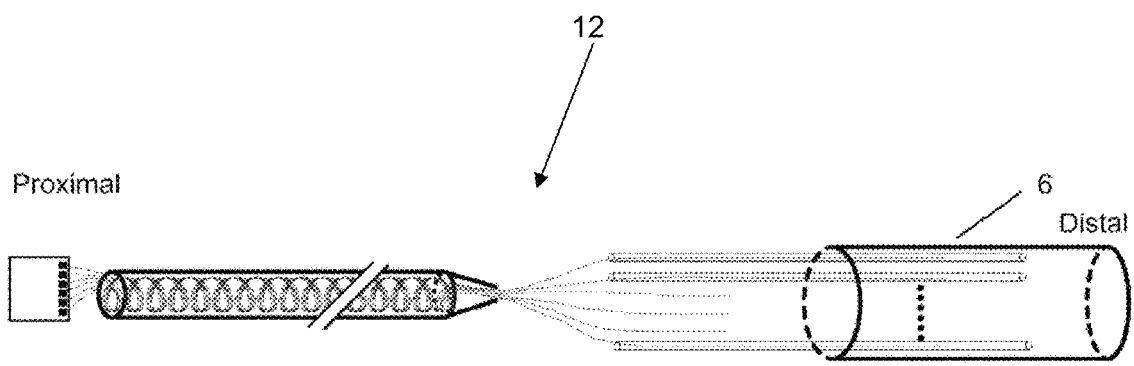
FIG. 4 illustrates individual ensheathed connecting elements encased in an end sheath.

FIG. 3 illustrates individual connecting elements ensheathed separately by individual protective sheaths 5. Each protective sheath 5 is preferably formed of a tube of biocompatible material. This ensheathing of individual connecting elements 3 permits separation of individual electrode contacts. The length of the connecting elements 3 may be varied. The individual ensheathing tubes (e.g., the protective sheaths 5) extend beyond the electrode so that the terminal ends can be bundled together with an end sheath 6 as illustrated in FIG. 4. The end sheath 6 is preferably formed of a tube of biocompatible material. The end sheath 6 preferably forms a snug fit around all of the individual ensheathed connecting elements 3. The end sheath 6 preferably allows the individual connecting elements 3 to remain in a single manageable bundle.

Figure 5:
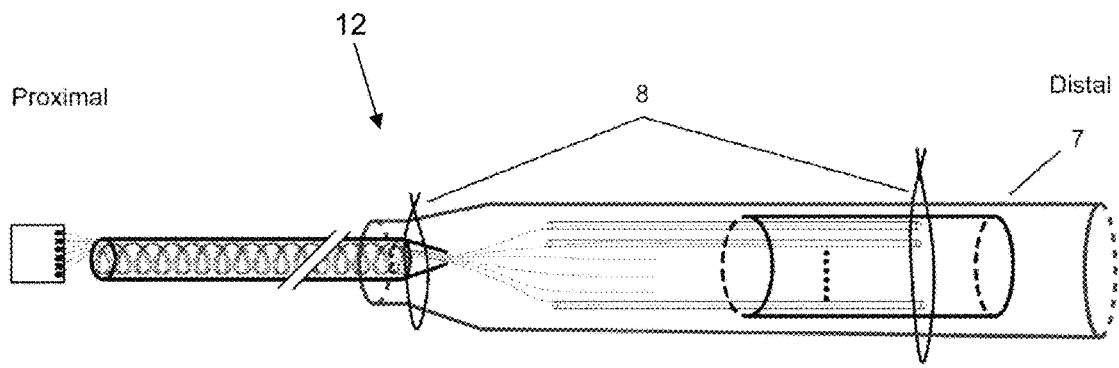
FIG. 5 illustrates a protective outer sheath that overlaps the coil sheath on one end of the multi-electrode lead and extends beyond the end sheath on the other end, the outer sheath being secured with circumferential sutures.
Figure 6:
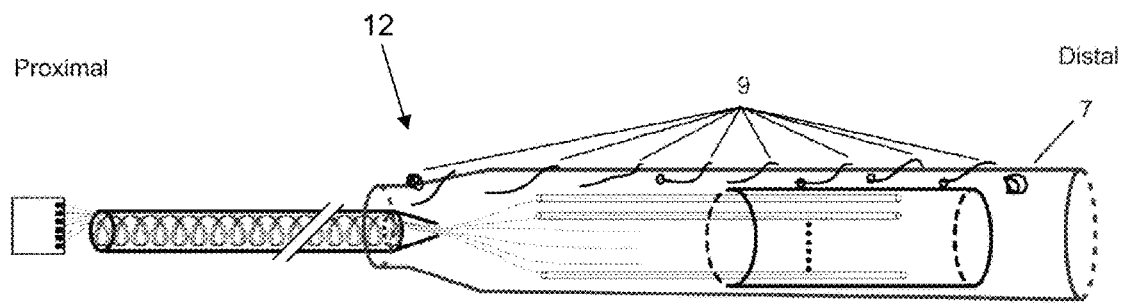
FIG. 6 illustrates a protective outer sheath that overlaps the coil sheath on one end of the multi-electrode lead and extends beyond the end sheath on the other end, the outer sheath being secured with running sutures.

FIG. 5 illustrates a protective biocompatible tube forming an outer sheath 7 that overlaps the coil sheath 4 on one end of the multi-electrode lead 12 and extends beyond the end sheath 6 on the other end. This outer sheath 7 is preferably a slit tube that allows insertion of the multiple ensheathed connecting elements 3. The outer sheath 7 may be closed using different methods. One method is to use circumferential sutures 8 applied over the end sheath 6 and the coil sheath 4 portions of the lead 12 such that direct compression force is not applied to the individual connecting elements 3. Another method, which is illustrated in FIG. 6, is to use a continuous run threaded suture 9, which may be aligned longitudinally along the bundle, and which may be easily unraveled during surgery.

Figure 7:
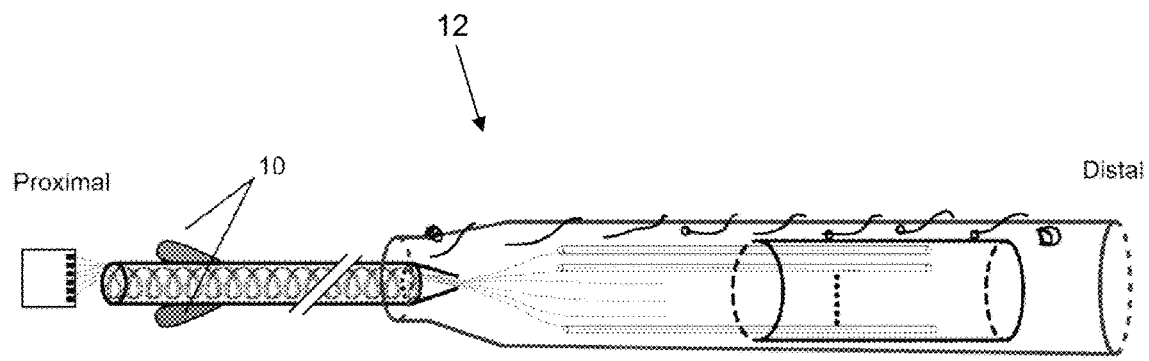
FIG. 7 illustrates flap like structures attached to the coil sheath.
Figure 8:
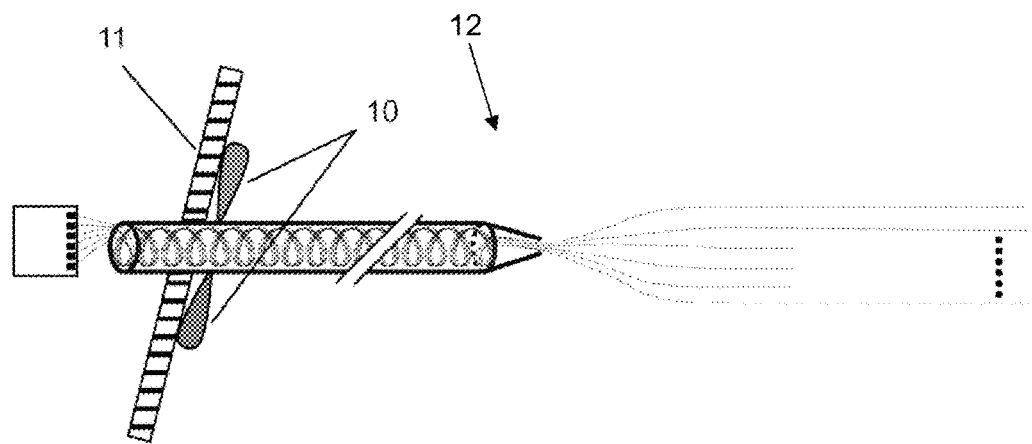
FIG. 8 illustrates use of the flap like structures, the flap like structures being spread open after insertion, thereby providing a barrier for exteriorizing of the lead through the skin.

FIG. 7 illustrates flap like structures, such as flaps 10, that are attached to the coil sheath 4. These flaps 10 may be made of biocompatible material, such as silicone, and may be pre-attached to the coil sheath 4 either during the process of making the coil sheath 4 tube or with a medical adhesive. The flaps 10 are pliable and preferably approximately 300 to 500 microns in thickness allowing them to be easily bent. These flaps 10 can be sutured to fascia or other tissue through or near which the lead 12 is being tunneled to anchor the lead. For percutaneous leads, the flaps 10 may be positioned on the portion of the lead adjacent to the inner surface of the skin. On insertion of the lead 12, the flaps 10 may be spread by the inner surface of the skin, as illustrated in FIG. 8, thereby providing a barrier for exteriorizing of the lead 12 through the skin 11. The flaps 10 also provide a barrier for migration of external infectious agents into the body. The flaps 10 can be coated with antibacterial, anti-inflammatory agents during the lead insertion process.

Figure 9:
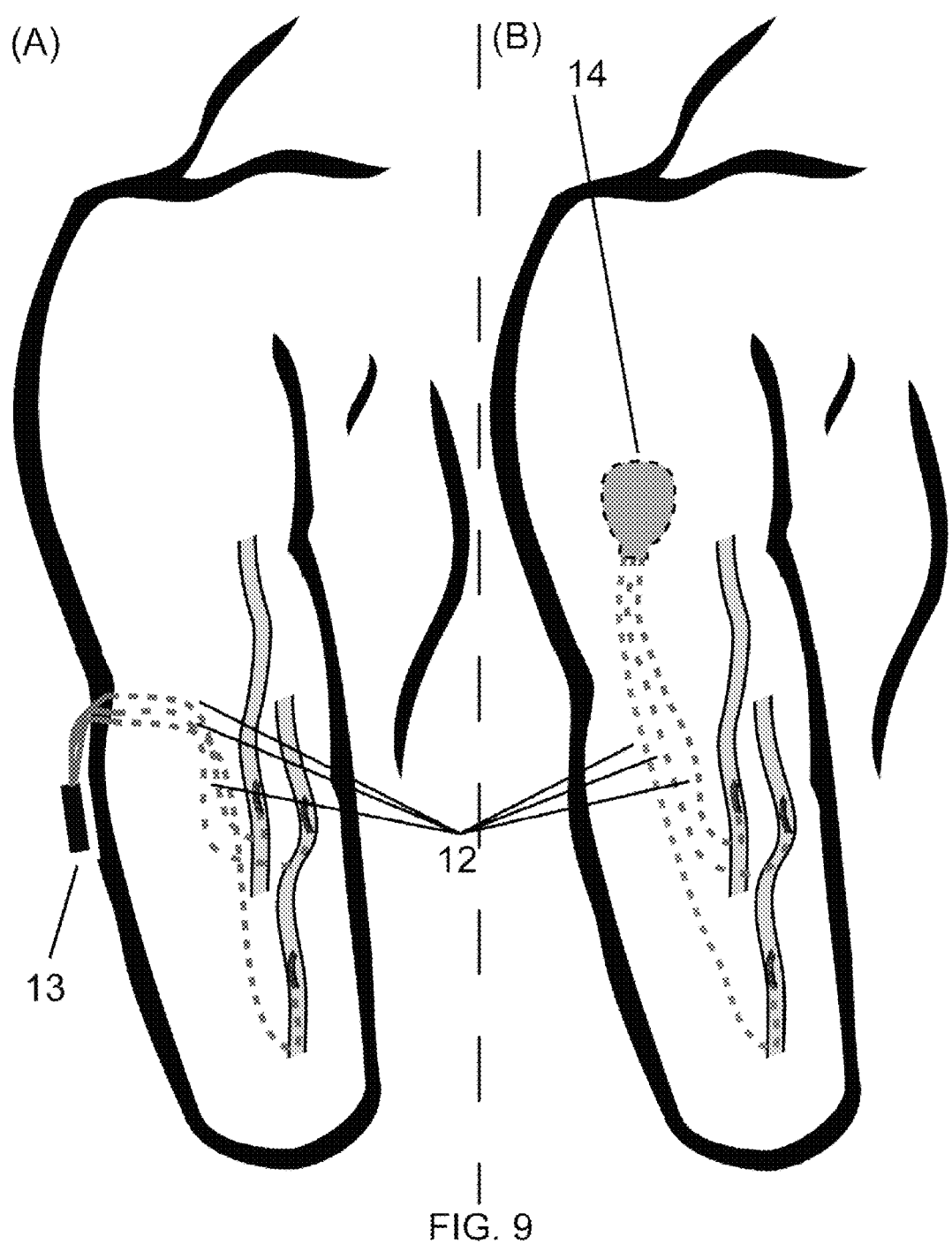
FIG. 9 illustrates one example embodiment of a multi-lead multi-electrode management system, where connecting elements are longitudinal intrafascicular electrodes (LIFE) and multiple multi-electrode leads are connected to an external connector and to an implantable pacemaker.

As illustrated in FIGS. 9A and 9B, multiple such multi-electrode leads 12 can be prepared with their proximal ends connected to a single device, such as an external connector 13 or an implantable pacemaker 14.

For deployment, individual multi-electrode leads 12 are routed to the vicinity of the target site for the electrode contact. The sutures 8 and/or 9 securing the outer sheath 7 are removed and the individual connecting elements 3 with their protective sheaths 5 and end sheath 6 are lifted along the slit portion of the outer sheath 7, which is discarded. Each individual connecting element 3 may be removed from the end sheath 6 as needed. The individual protective sheath 5 from the connecting element 3 is removed and the electrode 1, electrode array, or distal end is anchored to and/or inserted into the targeted tissue.

In one embodiment, a multi-lead multi-electrode system including one or more of the multi-electrode leads 12 may be used for recording peripheral nerve motor activity from multiple nerves at multiple sites using longitudinal intrafascicular electrodes. In such a distributed intrafascicular multi-electrode (DIME) system, there may be multiple leads targeting multiple nerves, where each multi-electrode lead is made up of 6 connecting elements. The connecting element consists of a Pt—Ir (90-10) wire of 25.4 µm diameter coated with biocompatible PTFE material of 7.6 µm thickness. Each Pt—Ir wire may be encased in a protective sheath consisting of a biocompatible polyimide tube of 160 microns inner and 179 micron outer diameter. Six such elements may be encased in an end sheath formed of a biocompatible silicone tube of 508 micron inner diameter and 940 micron outer diameter. The coil sheath formed of a biocompatible silicone tube has inner and outer diameters of 300 and 600 microns, respectively. The outer sheath formed of a biocompatible silicone tube has a 1400 microns inner diameter and 2000 microns outer diameter.

Figure 10:
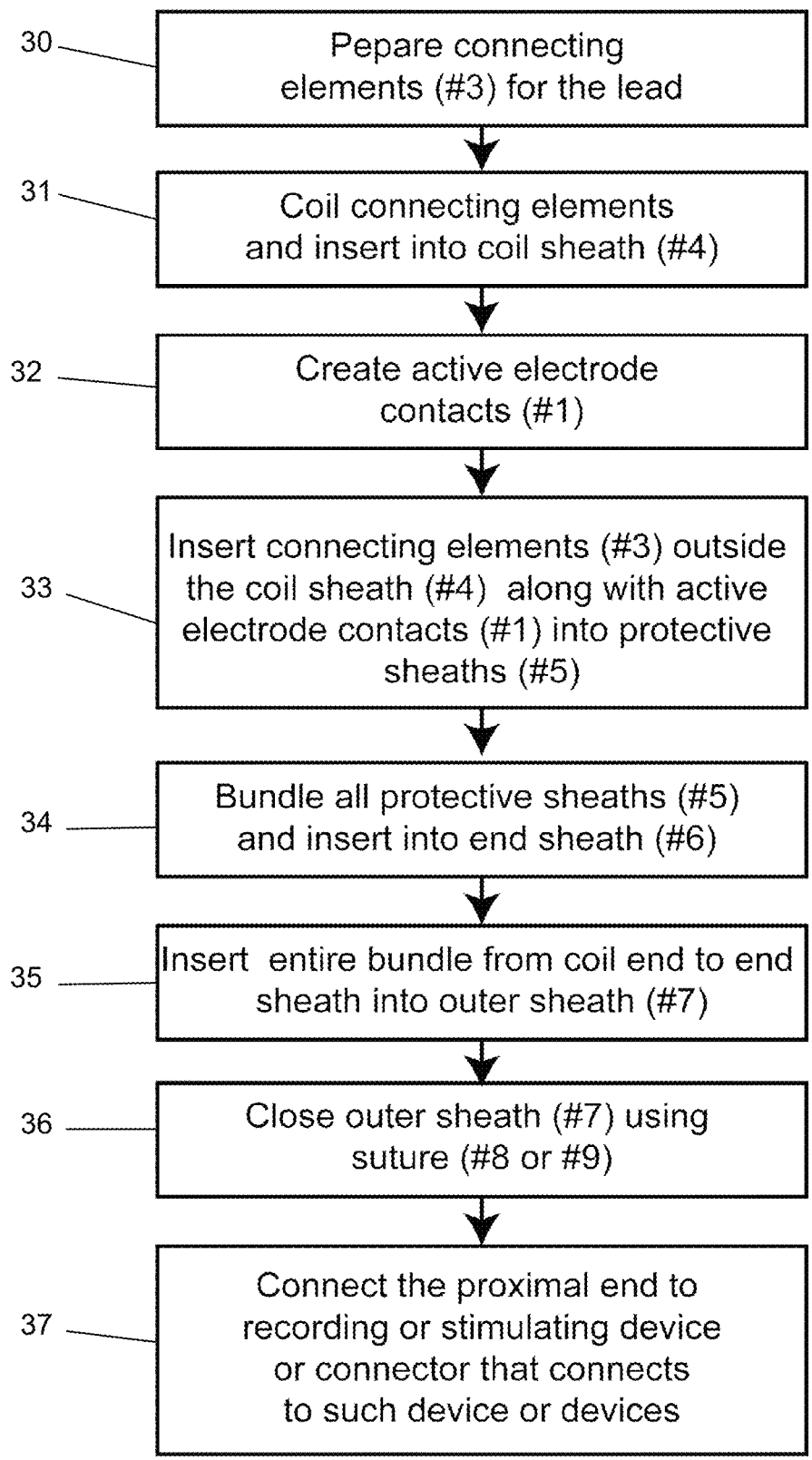
FIG. 10 illustrates a method steps for fabricating a multi-electrode lead.

FIG. 10 illustrates method steps for a typical process of fabricating the lead 12. At 30, elements 3 are prepared for connecting to the lead 12. At 31, the connecting elements 3 are coiled and inserted into the coil sheath 4. At 32, the active electrode contacts 1 are created. At 33, the connecting elements 3 and the active electrode contacts 1 outside of the coil sheath 4 are inserted into the protective sheath 5. At 34, all of the protective sheaths 5 are bundled together and inserted into the end sheath 6. At 35, the entire bundle, from the coil end to the end sheath 6, is inserted into the outer sheath 7. At 36, the outer sheath 7 is closed, for example, with the suture 8 and/or 9. At 37, the proximal end is connected to an operative device 14, such as a recording device or a stimulating device, or to a connector that connects to such an operative device.

Figure 11:
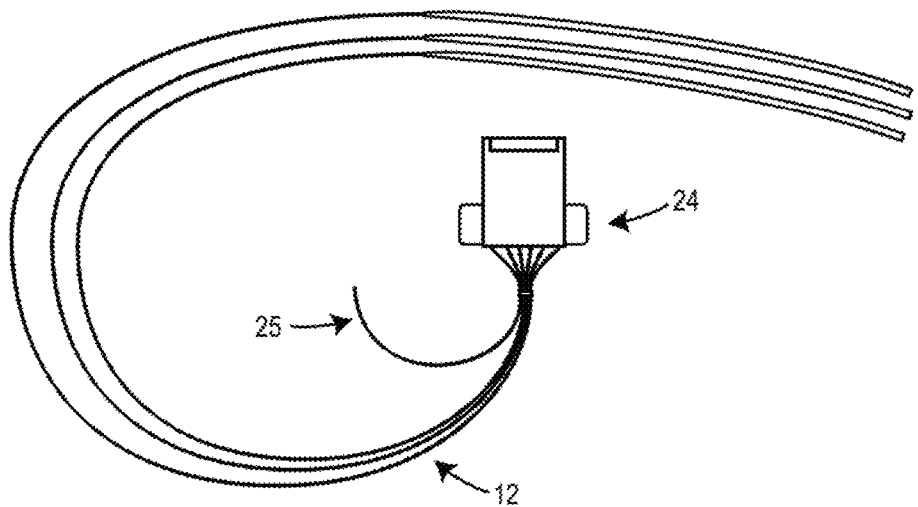
FIG. 11 illustrates a prototype of distributed intrafascicular multi-electrode (DIME) system.

FIG. 11 illustrates one preferred embodiment of a multi-lead multi-electrode management system constructed in accordance with the teachings of this disclosure. In this arrangement, a separate ground electrode 25 that is not part of the packaged lead 12 is also illustrated. At least one, and preferably more than one of the multi-electrode leads 12 are connected to the operative device 24. Further, the ground electrode 25 is operatively connected with one or more of the multi-electrode leads 12. However, a multi-lead multi-electrode management system is not limited to the components shown in FIG. 11, and may include additional components or fewer components.

Figure 12:
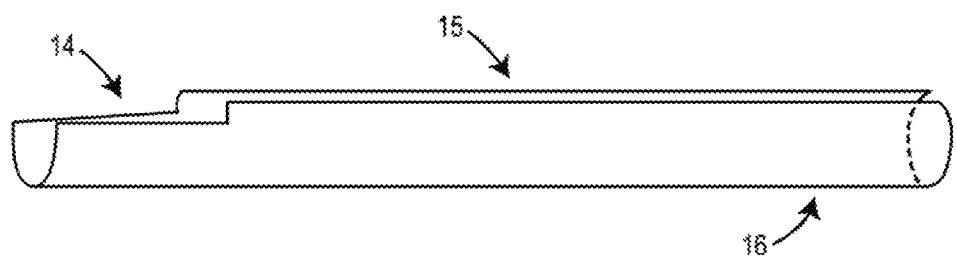
FIG. 12 illustrates the outer sheath of FIG. 5.

As illustrated in FIG. 12, the outer sheath 7 of FIG. 5 may be prepared by first making a transverse cut 14 at the proximal end and subsequently slitting the outer sheath longitudinally along its length 15.

Figure 13:
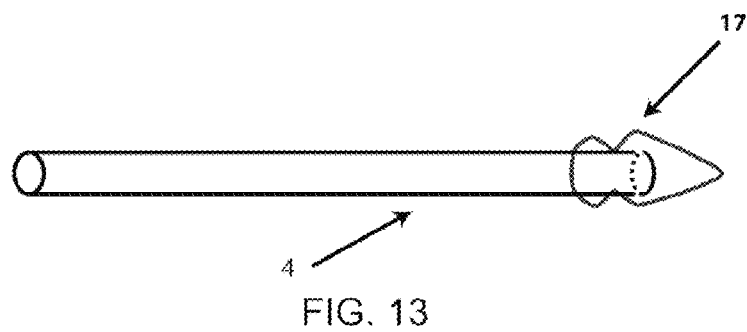
FIG. 13 illustrates the coil sheath.

As illustrated in FIG. 13, the coil sheath 4 may have an anchoring structure 17 at its distal end. The anchoring structure 17 serves to hold the suture 8 or 9 securing the outer sheath 7 to coil sheath 4 in place. In the illustrated embodiment, the anchoring structure 17 has an "arrow head" shape including a raised circumferential "ridge" like structure with a conical tip. The ridge structure is preferably formed by patterning silicone on top of the coil sheath.

Figure 14:
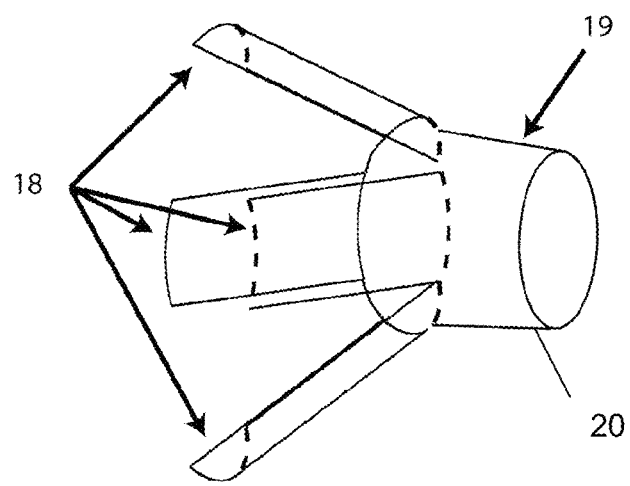
FIG. 14 illustrates a flap arranged in the form of a petal anchor.

FIG. 14 illustrates one exemplary arrangement of the flaps 10 of FIGS. 7 and 8, the flaps 10 having the form of a petal anchor 19. The petal anchor 19 can be fabricated using any flexible tube like structure, preferably made out of biocompatible material. In one embodiment, the petal anchor 19 is fabricated using a silicone tube as illustrated in FIG. 14. One end of the tube is split into 3 or more parts of desired length along its length to form multiple petal like structures 18 extending from a base portion 20. The parts 18 are preferably equally sized. The petal base 20 can be reinforced by adding an additional layer of silicone.

Figure 15:
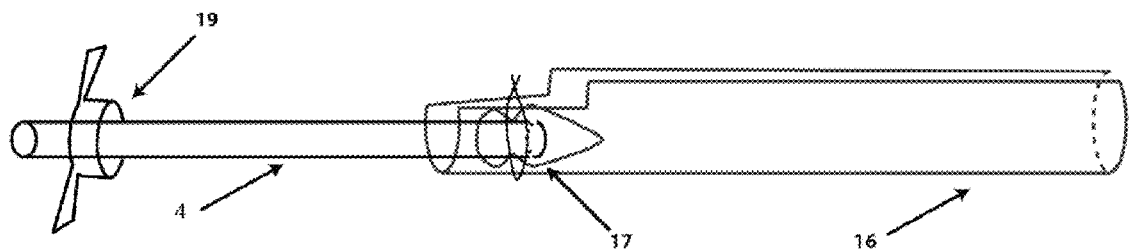
FIG. 15 illustrates a fully assembled coil sheath.
Figure 16:
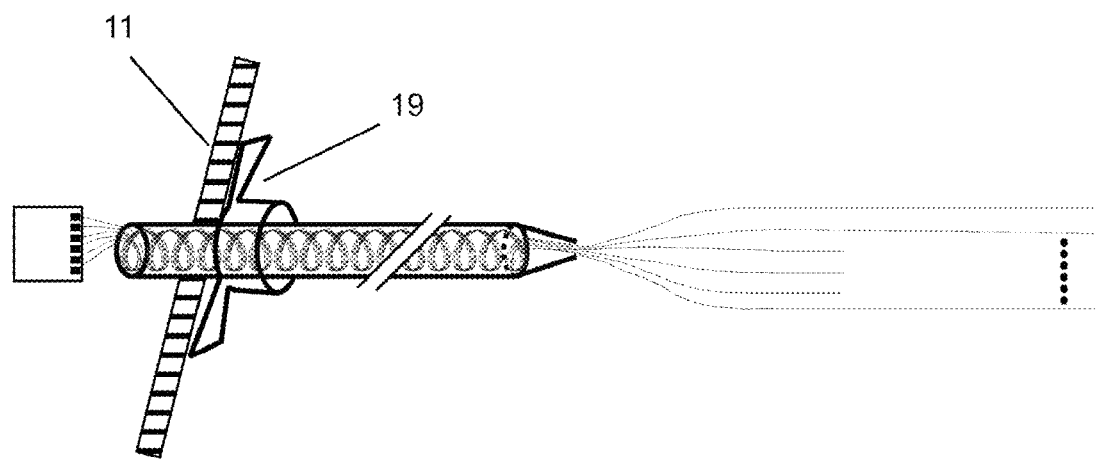
FIG. 16 illustrates the multi-electrode lead with the petal anchor of FIG. 14.

FIG. 15 illustrates a fully assembled coil sheath 4 with a "ridge" like structure 17 at the distal end, and the petal anchor 19 at the proximal end. During percutaneous implantation, for example into a human patient, the petal like structures 18 the petal anchor 19 open up once the coil sheath 4 is pushed across the skin 11, as illustrated in FIG. 16. Once open, the anchor 19 serves to reduce the in-out movement of the lead into and/or out of the patient, thereby minimizing the chance of infection due to "pistoning" effect. The petal anchor 19 also provides a barrier for exteriorizing of the lead 12 through the skin 11.

Figure 17:
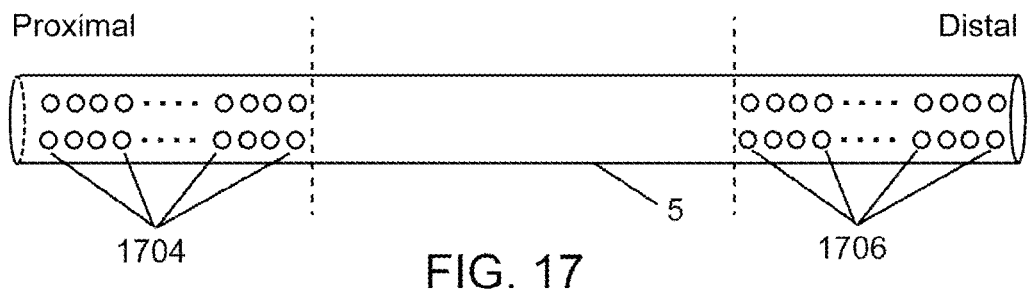
FIG. 17 illustrates an individual protective sheath along with proximal and distal apertures.

FIG. 17 illustrates an individual protective sheath 5 along with proximal 1704 and distal 1706 apertures. As previously illustrated in FIG. 3, individual connecting elements 3 may each be ensheathed by individual protective sheaths 5 that may comprise a tube of biocompatible material. Sterilization of connecting elements 3 is required in order to introduce them in a human body and is achieved by adequate penetration of a sterilization agent into the space between the protective sheath 5 and connecting elements 3. As illustrated in FIG. 17, in order to allow the sterilization agent to reach the connecting elements 3, apertures 1704, 1706 are introduced to the protective sheathes 5.

Apertures 1704, 1706 may be distributed along the entire length of the protective sheath 5 or over defined lengths of the protective sheath 5. In one embodiment, the protective sheaths 5 are manufactured of a biocompatible polyimide tube of approximately 160 microns inner and 170 microns outer diameter and the length of the tube 5 is approximately 150 millimeters. Apertures 1704, 1706 may be laser drilled for the first quarter or proximal end, and last quarter or distal end, of the protective sheath 5, covering approximately 4.5% of the surface area of the protective sheath 5. In this embodiment, there are no apertures in the middle portion of the sheath 5.

In one embodiment, a total of 12,000 apertures 1704, 1706 may be drilled, 600 on each end of the protective sheath 5. In one straight line at the proximal and distal ends, 1500 apertures of approximately 15 µm diameter are drilled with 50 μm distance between the apertures. This pattern may be repeated around the circumference of the tubing at approximately 45 degrees for a total of 8 lines of apertures along the length of the protective sheath 5. The apertures 1704, 1706 facilitate penetration of the sterilization agent from either end of the protective sheath 5 and allow sufficient diffusion of the sterilization agent to the middle half of the sheath 5. The solid surface of the central portion of the sheath 5 (e.g., the section without apertures) offers stiffness and improves the manipulation and management of the individual highly flexible connecting elements 3 inserted into the protective sheath 5 during deployment and implantation.

Figure 18:
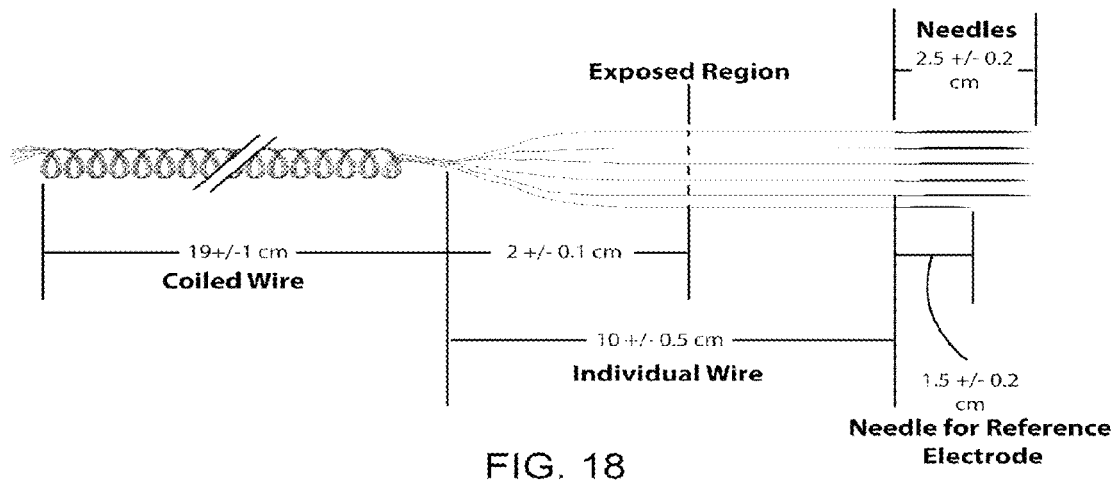
FIG. 18 illustrates dimensions for one exemplary embodiment of the system of FIG. 1.
Figure 19:
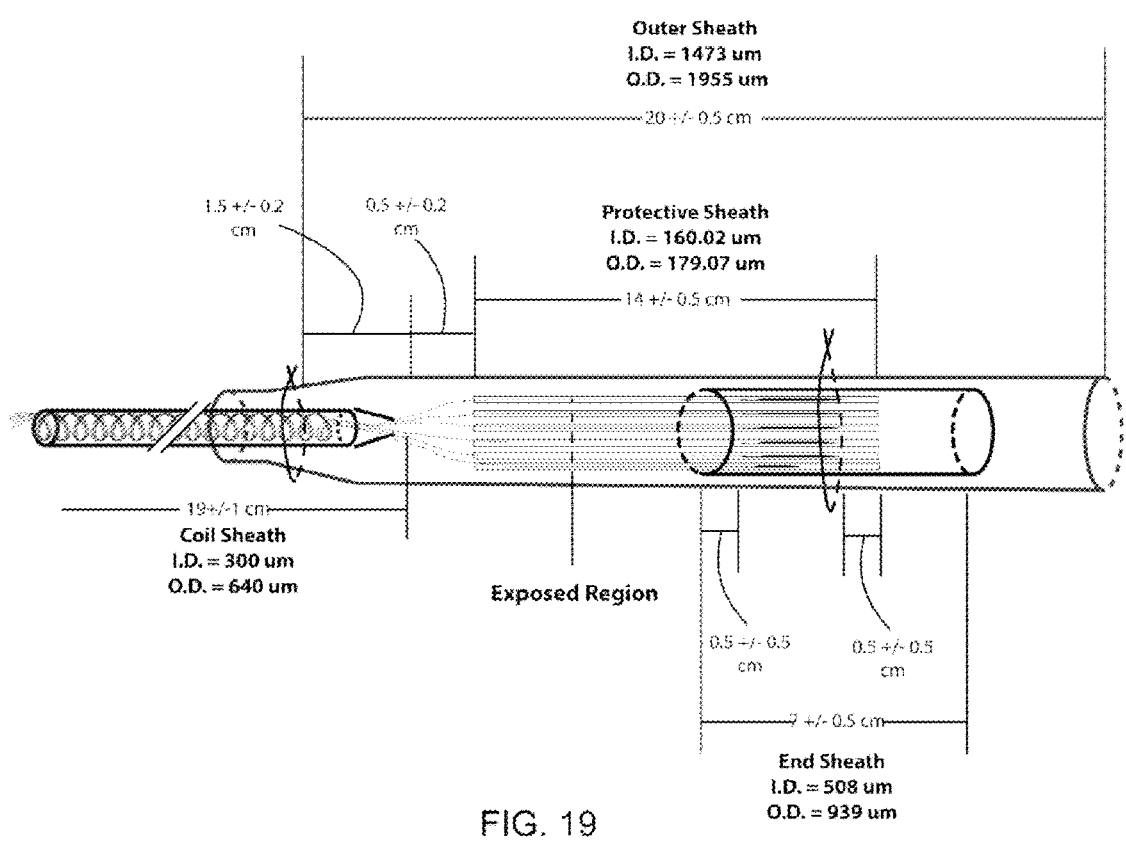
FIG. 19 illustrates dimensions for one exemplary embodiment of the system of FIG. 5.

FIG. 18 illustrates approximate dimensions in centimeters (cm) for one embodiment of the system illustrated in FIG. 1, while FIG. 19 illustrates approximate dimensions for one embodiment of the system illustrated in FIG. 5. Other dimensions may be used depending on the particular application involved.

In other exemplary arrangements, connecting elements 3 may be micro fiber-optic cables for optical stimulation connected to different types of electrodes, such as thin film longitudinal intrafascicular electrodes (tfLIFE), transverse intrafascicular multichannel electrodes (TIME), flat interfaced nerve electrodes (FINE), and other electrode configurations or combinations of two different electrode configurations as would be well understood in the art.

A multi-electrode lead, multi-lead multi-electrode management system, and/or method of making a multi-electrode lead in accordance with the teachings of the present disclosure may be useful in one or more ways, including but not limited to:

1. Multi-site gastric muscle/enteric nerve stimulation, recording and simultaneous stimulation and recording for treatment of gastroparesis, obesity, dysmotility and other gastric disorders;
2. Multi-site stimulation of peripheral, cranial and spinal nerves for pain management;
3. Multi-site stimulation of peripheral nerves for sensory feedback from prostheses or other external device with sensing elements;
4. Multi-site recording from peripheral nerves for identifying multiple motor intents for potential use in control of prostheses;
5. Multi-site stimulation of multiple muscles, such as intercostal muscles, abdominal muscles and diaphragm for respiratory assistance;
6. Multi-site stimulation of phrenic nerves (left and right) for phrenic pacing for respiratory assistance;
7. Multi-site stimulation of nerves for functional electrical stimulation after paralysis for activities such as hand grasp, pinch, standing, walking;
8. Multi-site recording from multiple muscles using implanted electrodes for control of prostheses;
9. Multi-site recording and/or stimulation of nerve or muscle tissue involved in the control of bladder and/or bowel function; and
10. Multi-site recording and/or stimulation of nerve or muscle tissue involved in the control of the spleen or other organs involved in the immune system or other systems that are innervated by autonomic nervous system tissue.

The multi-electrode lead, multi-lead multi-electrode management system, and/or method of making a multi-electrode lead of the present disclosure in some arrangements may provide solutions for various practical hurdles posed by the commercially available multi-electrode leads. For example, current commercially available multi-electrode leads are typically a single macro lead that connects to electrode contacts that are evenly placed in concentric circles. This type of configuration of lead is not possible to implant in micro structures such as peripheral or cranial nerves or implanting in soft movable structures such as gastric muscles. The proposed packaging process for multi-electrode systems of the present disclosure, however, would facilitate in some arrangements targeting peripheral or cranial nerves, gastric and other nerve or muscle tissues that are spatially distributed over a large area or span various organs.

In another example, in commercially available multi-electrode leads, the inter-electrode distance is pre-determined. Intraoperatively, the only way the inter-electrode distance can be changed is by choosing different pairs of electrodes. In the proposed multi-electrode lead configuration of the present disclosure, however, there is in some arrangements full flexibility of specifying the intra-electrode distance at the time of implantation.

In a further example, packaging according to the teachings of the present disclosure in some arrangements can prevent or minimize entanglement of individual connecting elements.

Additionally, packaging according to the teachings of the present disclosure in some arrangements allows management of the lead and connecting elements during a surgical procedure.

We claim:

1. A multi-electrode lead comprising:
  a plurality of electrodes;
  a plurality of elongate connecting elements, each connecting element having a distal end and a proximal end, the distal end of each connecting element being operatively connected to one of the plurality of electrodes and separate connecting elements being operatively connected to different electrodes, at least two of the connecting elements being secured together in a bundle between the distal and proximal ends; and
  a coil sheath, the bundle being ensheathed in the coil sheath,
  wherein the electrodes and the distal ends of the connecting elements are separated or readily separable such that the electrodes are adapted to be applied to a plurality of different nerve and/or muscle tissues spaced apart across a region where multiple muscles or multiple nerves interact on a patient, and
  wherein the bundle of elongate connecting elements is coiled over a partial length thereof within the coil sheath to provide strain relief and to provide flexibility.

2. The multi-electrode lead of claim 1, further comprising a plurality of protective sheaths, wherein each connecting element is ensheathed separately by at least one of the protective sheaths.

3. The multi-electrode lead of claim 2, wherein each of the plurality of protective sheaths comprise a tube including a plurality of apertures.

4. The multi-electrode lead of claim 1, further comprising an outer sheath, wherein the outer sheath encases a portion of the connecting elements and the electrodes, and optionally wherein the outer sheath includes a first end that overlaps the coil sheath and a second end that extends beyond the end sheath.

5. The multi-electrode lead of claim 4, wherein the outer sheath is in the form of slit tube.

6. The multi-electrode lead of claim 5, wherein the slit tube comprises an elongate tube having an axis extending from a first end to a second end a longitudinal slit extending from the first end to the second end.

7. The multi-electrode lead of claim 5, wherein the slit tube is closed around the connecting elements with one of a circumferential suture and a continuous run longitudinal suture.

8. The multi-electrode lead of claim 1, further comprising one or more flaps attached to the coil sheath.

9. The multi-electrode lead of claim 8, wherein the flaps are pliable and disposed adjacent the proximal ends of the connecting elements.

10. The multi-electrode lead of claim 8, wherein the flaps are coated with antibacterial and/or anti-inflammatory agents.

11. A multi-electrode lead comprising:
   a plurality of electrodes;
   a plurality of elongate connecting elements, each connecting element having a distal end and a proximal end, the distal end of each connecting element being operatively connected to one of the plurality of electrodes;
   a plurality of protective sheaths, each connecting element being ensheathed separately by at least one of the protective sheaths; and
   an end sheath, terminal ends of the protective sheaths extending beyond the distal ends of the connecting elements and the electrodes, the terminal ends of the protective sheaths being bundled together within the end sheath and are surrounded by the end sheath;
   wherein at least two of the connecting elements are secured together in a bundle between the distal and proximal ends, and
   wherein the electrodes and the distal ends of the connecting elements are separated or readily separable such that the electrodes are adapted to be applied to a plurality of different nerve and/or muscle tissues spaced apart across a region where multiple muscles or multiple nerves interact region on a patient.

12. A multi-lead multi-electrode system, comprising:
    the multi-electrode lead of claim 1.

13. The multi-lead multi-electrode system of claim 12, further comprising a ground electrode operatively connected with one or more of the multi-electrode leads.

14. The multi-lead multi-electrode system of claim 12, further comprising an operative device or a connector, wherein one or more of the multi-electrode leads is operatively connected at the proximate end thereof to the operative device or connector, and wherein the electrodes and the distal ends of the connectors are free for securement to one or more muscle or nerve tissues.

15. The multi-lead multi-electrode system of claim 12, further comprising one or more flaps attached to a coil sheath, wherein the flaps comprise a petal anchor.

16. The multi-lead multi-electrode system of claim 12, further comprising a coil sheath, wherein the bundle is ensheathed in the coil sheath, wherein the coil sheath has an anchoring structure, preferably at its distal end, wherein said anchoring structure is arranged to hold the suture securing the outer sheath to coil sheath in place.

17. The multi-lead multi-electrode system of claim 16, wherein the anchoring structure has an arrow head shape.

\* \* \* \* \*